(12) United States Patent
Shigyo et al.

(10) Patent No.: US 11,242,655 B2
(45) Date of Patent: Feb. 8, 2022

(54) PAPER TREATMENT AGENT

(71) Applicant: Miyoshi Oil & Fat Co., Ltd., Tokyo (JP)

(72) Inventors: Emi Shigyo, Aichi (JP); Kiyoshi Taira, Aichi (JP)

(73) Assignee: MIYOSHI OIL & FAT CO., LTD., Tokyo (JP)

(*) Notice: Subject to any disclaimer, the term of this patent is extended or adjusted under 35 U.S.C. 154(b) by 0 days.

(21) Appl. No.: 16/765,559

(22) PCT Filed: Oct. 15, 2018

(86) PCT No.: PCT/JP2018/038327
§ 371 (c)(1),
(2) Date: May 20, 2020

(87) PCT Pub. No.: WO2019/106985
PCT Pub. Date: Jun. 6, 2019

(65) Prior Publication Data
US 2020/0308770 A1   Oct. 1, 2020

(30) Foreign Application Priority Data

Nov. 30, 2017  (JP) .............................. JP2017-230759

(51) Int. Cl.
| | | |
|---|---|---|
| *D21H 21/24* | (2006.01) | |
| *D21H 17/06* | (2006.01) | |
| *D21H 17/09* | (2006.01) | |
| *D21H 17/10* | (2006.01) | |
| *D21H 17/14* | (2006.01) | |
| *D21H 27/00* | (2006.01) | |
| *A47K 10/16* | (2006.01) | |

(52) U.S. Cl.
CPC ............ *D21H 21/24* (2013.01); *D21H 17/06* (2013.01); *D21H 17/09* (2013.01); *D21H 17/10* (2013.01); *D21H 17/14* (2013.01); *D21H 27/002* (2013.01); *A47K 10/16* (2013.01)

(58) Field of Classification Search
USPC .......................................................... 162/179
See application file for complete search history.

(56) References Cited

U.S. PATENT DOCUMENTS

| | | |
|---|---|---|
| 2007/0219107 A1 | 9/2007 | Nonomura et al. |
| 2011/0024066 A1 | 2/2011 | Matsumura et al. |
| 2013/0101817 A1 | 4/2013 | Iwasaki |
| 2021/0047783 A1* | 2/2021 | Shigyo .................. D21H 21/22 |

FOREIGN PATENT DOCUMENTS

| | | |
|---|---|---|
| JP | 10-226986 | 8/1998 |
| JP | 2001-11790 | 1/2001 |
| JP | 2006-45097 | 2/2006 |
| JP | 2007-107173 | 4/2007 |
| JP | 2009-84240 | 4/2009 |
| JP | 2009-263837 | 11/2009 |
| JP | 2012-10907 | 1/2012 |
| JP | 2014-208921 | 11/2014 |
| JP | 2016-74999 | 5/2016 |

OTHER PUBLICATIONS

JP 2009-084240 A, Matsui Tadashi, Kracie Home Products Ltd., Apr. 2009, machine translation.*
International Search Report (ISR) dated Nov. 13, 2018 in International (PCT) Application No. PCT/JP2018/038327.

* cited by examiner

*Primary Examiner* — Mark Halpern
(74) *Attorney, Agent, or Firm* — Wenderoth, Lind & Ponack, L.L.P.

(57) ABSTRACT

Provided is a paper treatment agent in which a polyhydric alcohol as a moisturizer has been mixed, and with which paper that has a favorable texture when pressed strongly against the skin as in the case of blowing the nose or the like, suppresses the moisture absorption and moisture desorption even under the environment of high humidity or low humidity, and retains the sense of use, the moist feeling, and the softness can be obtained.

4 Claims, No Drawings

PAPER TREATMENT AGENT

This application is a 371 of PCT/JP2018038327 filed on 15 Oct. 2018

TECHNICAL FIELD

The present invention relates to a paper treatment agent.

BACKGROUND ART

Conventionally, a product of paper, to which a better moist feeling and better softness are imparted as compared with those of ordinary dry tissues by treating the paper with a paper treatment agent containing a moisturizer as a main component, is known. A lotion tissue, which is a typical product in the above product, is a moisturizing tissue made by applying a lotion agent as a paper treatment agent onto tissue base paper. The lotion tissue is moist, and has a texture of softness and largely-improved sense of use, and therefore, the lotion tissue has been widespread as a seasonal product in winter for hay fever, a measure for influenza, and the like, and has been expanded from for use mainly for blowing the nose to for daily use, and has been becoming for year-round use.

As a moisturizer for a moisturizing tissue, a polyhydric alcohol such as glycerin, or polyethylene glycol (PEG), in particular, glycerin that is a moisturizer being inexpensive and excellent in safety is used in many cases.

By using the moisturizer, the hygroscopic property and moisture retaining property of paper are enhanced, and a soft and moist texture is imparted to the paper. A material texture felt by a person when touches a tissue and a texture of a tissue as a feel have a great effect on the sense of use of moisturizing tissues, and have become the most important quality for adding a value to the product.

For example, moisturizing tissues are used for blowing the nose in many cases, and it is desirable for a tissue to have a favorable texture when the tissue is pressed strongly against the skin as in the case of blowing the nose, in particular, to have a favorable slippery feeling, from the viewpoint of reducing the burden on the skin with a less irritating feel, and a reduction in the surface friction when pressure is applied on the tissue has been demanded.

Further, since a tissue has been used throughout the year, there has been a problem of, for example, not only deterioration in the texture under the environment of low humidity, specifically, feeling of reduction in the moist feeling and softness of a lotion tissue in a dry room as in winter in Japan, but also deterioration in the sense of use under the environment of high humidity, specifically, ease of tearing of a lotion tissue due to the reduced paper strength in a high humidity room as in summer in Japan. A lotion tissue is softened by taking moisture in the tissue with glycerin being a moisturizer, and by mixing a softening component into the tissue, and the softness of a moisturizing tissue is developed by the decrease in pulp/pulp hydrogen bonds due to the increase in the water content of coated paper. The water content taken into a tissue by a moisturizer depends on the humidity of the outer environment, and moisture is lost from a tissue under the environment of low humidity and hydrogen bonds between pulps are reconstructed, and therefore, paper becomes harder as compared with that under the environment of high humidity. In addition, a tissue absorbs excessively water under the environment of high humidity, and the paper strength is decreased.

Conventionally, the following techniques have been proposed as for a paper treatment agent.

In Patent Literature 1, a technique of mixing an oil substance and water-soluble wax together with a moisturizer into a paper treatment agent has been proposed. In the technique, stable retention of a tactile feeling such as smoothness has been attained, but there has been a problem that the water-soluble wax has high viscosity, impairs the fluidity and uniform application of an agent, and deteriorates the operability.

In Patent Literatures 2 to 4, a technique of mixing a sucrose fatty acid ester or a branched alcohol together with a moisturizer into a paper treatment agent has been proposed, and improvement of the softness and touch under the environment of low humidity has been attained. These bases have an advantage of being easily mixed into a moisturizer, and the softness can be somewhat retained even under the environment of low humidity, however, the effect has not been sufficiently exerted. In addition, a texture, in particular, a slippery feeling, which is specifically developed when the paper is pressed strongly against the skin as in the case of blowing the nose or the like, cannot be obtained.

CITATION LIST

Patent Literature

Patent Literature 1: JP 10-226986 A
Patent Literature 2: JP 2014-208921 A
Patent Literature 3: JP 2016-74999 A
Patent Literature 4: JP 2007-107173 A

SUMMARY OF INVENTION

Technical Problem

The present invention is made in consideration of the above circumstances, and an object of the present invention is to provide a paper treatment agent in which a polyhydric alcohol has been mixed as a moisturizer, and with which paper having a favorable texture when the paper is pressed strongly against the skin as in the case of blowing the nose or the like and having low outer humidity environmental dependence of a texture and the sense of use is obtained.

Solution to Problem

As a result of intensive studies to solve the problems described above, the present inventors have found that in a mixing system in which a polyhydric alcohol of a moisturizer is used as the main component, a paper treatment agent in which a straight chain alcohol or fatty acid, and an anionic surfactant have been used provides to pater a slippery feeling that is specifically developed when pressure is applied on the pater, suppresses the moisture absorption or the moisture desorption (hereinafter, may be abbreviated as absorption and desorption of moisture in some cases) even under the environment of high humidity or low humidity, and reduces the humidity environmental dependence of a texture of the pater, and thus the present inventors have completed the present invention.

That is, in order to solve the problems described above, the paper treatment agent according to the present invention is a paper treatment agent containing a polyhydric alcohol (A) as a main component, and is characterized in that the paper treatment agent contains at least one component (B) selected from a straight chain alcohol and a straight chain fatty acid, and an anionic surfactant (C), and in a case where the paper treatment agent contains at least one component (B') selected from a branched alcohol and a branched fatty acid, a mass ratio (B'/B) of the component (B') to the component (B) is less than 1.

Advantageous Effects of Invention

According to the present invention, paper, which has a unique texture when the paper is pressed strongly against the skin as in the case of blowing the nose or the like, that is, a slippery feeling that is specifically developed when pressure is applied on the paper, suppresses the absorption and desorption of moisture even under the environment of high humidity or low humidity, and retains the moist feeling, and the softness, can be obtained.

DESCRIPTION OF EMBODIMENTS

Hereinafter, the present invention will be described in detail.

In the paper treatment agent according to the present invention, a polyhydric alcohol of component (A) is a moisturizer that enhances the hygroscopic property and moisture retaining property of paper, and imparts a moist feeling to the paper, and is a main component of the paper treatment agent.

In this regard, the expression "main component" means that a component (A) is mixed in the largest mass among the respective additive components that are raw materials for a paper treatment agent. In particular, the amount of the component (A) to be added is preferably 50% by mass or more, more preferably 70% by mass or more, furthermore preferably 75% by mass, and still more preferably 80% by mass or more, relative to the whole amount of raw materials for the paper treatment agent except for water.

Examples of the polyhydric alcohol of component (A) to be used in the present invention include glycerin, diglycerin, triglycerin, polyglycerin, 1,2-propanediol, 1,3-propanediol, dipropylene glycol, polypropylene glycol, 1,3-butanediol, 1,4-butanediol, 1,2-pentanediol, 1,2-hexanediol, ethylene glycol, diethylene glycol, triethylene glycol, polyethylene glycol, polyoxyethylene glycerin ether, isoprene glycol, pentaerythritol, and trimethylolpropane. Further, as the polyhydric alcohol, sugar alcohols or saccharides may also be used. Examples of the sugar alcohols include sorbitol, inositol, glucosyl trehalose, xylitol, erythritol, mannitol, lactitol, fructose, oligosaccharide alcohol, maltitol, reduced palatinose, reduced sugar syrup, and reduced starch hydrolysate. Examples of the saccharides include fructose, glucose, lactose, xylose, psicose, maltose, starch syrup, oligosaccharide, maltose, trehalose, lactose, palatinit, sucrose, isomerized sugar syrup, isomalto-oligosaccharide, fructo-oligosaccharide, galacto-oligosaccharide, xylo-oligosaccharide, lactosucrose, soybean oligosaccharide, raffinose, stevia, licorice, saccharin, aspartame, acesulfame K, and sucralose. These may be used singly alone or in combination of two or more kinds thereof.

Among them, glycerin is preferred. In a case where glycerin is used as a moisturizer, the proportion of the glycerin to the whole amount of moisturizer is preferably 80% by mass or more, and more preferably 90% by mass or more. As the moisturizer to be used in combination with the glycerin, for example, sorbitol or the like can be mentioned.

In the paper treatment agent according to the present invention, as the moisturizer, a component other than the polyhydric alcohol of component (A) may also be used in combination with the component (A). As such a moisturizer, for example, amino acids, or alkalis/acids having hygroscopic property or salts thereof can be mentioned. Examples of the amino acids include glycine, valine, leucine, isoleucine, serine, threonine, phenylalanine, arginine, lysine, aspartic acid, glutamic acid, cystine, cysteine, methionine, and tryptophan. Examples of the alkalis/acids having hygroscopic property or salts thereof include pantetheine-S-sulfonate, trimethylglycine, betain, pyrophosphoric acid, sodium pyrophosphate, chondroitin sulfate, potassium pyrophosphate, hyaluronic acid, sodium hyaluronate, sodium metaphosphate, potassium polyphosphate, sodium pyrrolidone carboxylate, sodium lactate, sodium chloride, calcium chloride, sodium alginate, and sodium polyacrylate. These may be used singly alone or in combination of two or more kinds thereof.

In the paper treatment agent according to the present invention, a component (B) is at least one kind selected from a straight chain alcohol and a straight chain fatty acid. By the action of the component (B), paper, which has a unique texture when the paper is pressed strongly against the skin as in the case of blowing the nose or the like, that is, a slippery feeling that is specifically developed when pressure is applied on the paper, suppresses the absorption and desorption of moisture even under the environment of high humidity or low humidity, and retains the sense of use, the moist feeling, and the softness, can be obtained. Although it is not intended to limit the present invention, it is considered that the orientation of the component (B) having a straight chain and polarity in a treatment agent applied onto paper may be involved in these effects. The component (B) has a thickening effect when mixed in a polyhydric alcohol such as glycerin, but by being used in combination with an anionic surfactant of a component (C), an agent having low viscosity and high stability, and capable of performing uniform application on paper can be obtained, and the unique texture of paper when the paper is pressed strongly against the skin, and the effect of suppressing the absorption and desorption of moisture of paper under the environment of high humidity or low humidity are developed.

The number of carbon atoms in each of the straight chain alcohol and straight chain fatty acid of a component (B) is not particularly limited, and is, for example, 4 to 30.

Examples of the straight chain alcohol include butanol (4:0), pentanol (5:0), hexanol (6:0), heptanol (7:0), octanol (8:0), nonanol (9:0), decanol (10:0), lauryl alcohol (12:0), tridecyl alcohol (13:0), myristyl alcohol (14:0), pentadecyl alcohol (15:0), cetyl alcohol (16:0), palmitoleyl alcohol (16:1), stearyl alcohol (18:0), oleyl alcohol (18:1), linoleyl alcohol (18:2), linolenyl alcohol (18:3), arachidyl alcohol (20:0), behenyl alcohol (22:0), and lignoceryl alcohol (24:0). Note that the expression inside the parentheses indicates the number of carbon atoms on the left and the number of unsaturated bonds on the right. These may be used singly alone or in combination of two or more kinds thereof. For example, cetylstearyl alcohol, which is a mixture of approximately equal amounts of cetyl alcohol and stearyl alcohol, may be used.

Examples of the straight chain fatty acid include butyric acid (4:0), valeric acid (5:0), caproic acid (6:0), caprylic acid (8:0), pelargonic acid (9:0), capric acid (10:0), lauric acid (12:0), myristic acid (14:0), palmitic acid (16:0), palmitoleic acid (16:1), hiragonic acid (16:3), stearic acid (18:0), oleic acid (18:1), linoleic acid (18:2), linolenic acid (18:3), arachidic acid (20:0), behenic acid (22:0), erucic acid (22:1), lignoceric acid (24:0), selacholeic acid (24:1), cerotic acid (26:0), montanic acid (28:0), and melissic acid (30:0). Note that the expression inside the parentheses indicates the same as the above. These may be used singly alone or in combination of two or more kinds thereof.

The aliphatic group of a component (B) may be a saturated aliphatic group having no double bond or an unsaturated aliphatic group having a double bond, and in consideration of the unique texture of paper when the paper is pressed strongly against the skin and the suppression of absorption and desorption of moisture of paper under the environment of high humidity or low humidity, the aliphatic group is preferably a saturated aliphatic group.

In the paper treatment agent according to the present invention, the component (B) is preferably to be a straight chain higher alcohol or a straight chain higher fatty acid. The terms "higher alcohol" and "higher fatty acid" means an alcohol having 12 or more carbon atoms and a fatty acid having 12 or more carbon atoms, respectively in the present invention. The number of carbon atoms of the component (B) is preferably 12 to 22, more preferably 14 to 20, and most preferably 16 to 18. If the number of carbon atoms is 12 or more, there is no concern of an odor, and the effect of suppressing the absorption and desorption of moisture is also improved. If the number of carbon atoms is 22 or less, it is suitable in view of economical practicality and in that the texture of paper is less likely to be hardened.

Among the straight chain alcohol and the straight chain fatty acid, in consideration of the uniform application on paper of paper treatment agent being involved in the development of the texture of paper and the suppression of absorption and desorption of moisture of paper, and the viscosity of agent being involved in the stable and easy operability, a straight chain higher alcohol is preferred, and in particular, cetylstearyl alcohol is more preferred.

With a paper treatment agent having low viscosity, the transfer is ease and the handling ability is favorable, the control of the amount of the treatment agent to adhere to coated paper is easy, and the operability is favorable. Therefore, it is required to avoid the deterioration in the operability due to the increase in the viscosity. Addition of water-soluble wax, a water-soluble polymer, a gelling agent, and the like tends to cause the deterioration in the operability due to the increase in the viscosity, however, the paper treatment agent according to the present invention in which a component (B) and a component (C) have been mixed in combination enables stable and easy operation.

The paper treatment agent according to the present invention may contain at least one kind (B') selected from a branched alcohol, and a branched fatty acid, and in that case, the mass ratio (B'/B) of the component (B') to the component (B) is less than 1, preferably 0.8 or less, more preferably 0.5 or less, furthermore preferably 0.1 or less, and most preferably 0.05 or less. If the mass ratio (B'/B) of the component (B') to the component (B) is increased, an effect due to the combination of the component (B) and the component (C), in particular, due to the action of the component (B), an effect of obtaining paper that has a unique texture when the paper is pressed strongly against the skin as in the case of blowing the nose or the like, that is, a slippery feeling that is specifically developed when pressure is applied on the paper, suppresses the absorption and desorption of moisture even under the environment of high humidity or low humidity, and retains the moist feeling, and the softness, can be hardly obtained.

In this regard, the number of carbon atoms of the component (B') is 6 or more, and particularly 8 to 22, and the number of carbon atoms of the branched chain is, for example, 1 to 10. The branched alcohol and the branched fatty acid of the component (B') are ordinary a monohydric alcohol and a monohydric fatty acid, respectively. Examples of the branched alcohol of the component (B') include 2-methyl-hexyl alcohol, 5-methyl-hexyl alcohol, 2-methyl-heptyl alcohol, 6-methyl-heptyl alcohol, 2-methyl-octyl alcohol, 7-methyl-octyl alcohol, 2-methyl-nonanol, 8-methyl-nonanol, 2-methyl-decyl alcohol, 9-methyl-decyl alcohol, 2-methyl-undecyl alcohol, 10-methyl-undecyl alcohol, 2-methyl-dodecyl alcohol, 2-hexyl-dodecyl alcohol, 11-methyl-dodecyl alcohol, 2-4-6-8-tetramethyl-nonanol, 5-methyl-hexanol, 2-methyl-pentadecyl alcohol, 14-methyl-pentadecyl alcohol, 2-methyl-heptadecyl alcohol, 2-heptyl-undecyl alcohol, 2-octyl-decyl alcohol, 16-methyl-heptadecyl alcohol, and isotridecyl alcohol. As the branched fatty acid, for example, a branched fatty acid obtained by replacing the —COH moiety of the branched alcohol described above with a carboxyl group —COOH can be mentioned.

In the paper treatment agent according to the present invention, in consideration of the unique texture of paper when the paper is pressed strongly against the skin and the suppression of absorption and desorption of moisture of paper under the environment of high humidity or low humidity, the content of the component (B) is preferably 0.05% by mass or more, more preferably 0.1% by mass or more, furthermore preferably 0.2% by mass or more, and particularly preferably 0.4% by mass or more, relative to the whole amount of the treatment agent except for water. Further, in consideration of the overall development of respective effects including operability, the content of the component (B) is preferably 20% by mass or less, more preferably 15% by mass or less, and furthermore preferably 10% by mass or less, relative to the whole amount of the treatment agent except for water. From the viewpoint of the unique texture of paper when the paper is pressed strongly against the skin, the content of the component (B) is particularly preferably 0.2% by mass or more, and in particular, most preferably 0.4% by mass or more, relative to the whole amount of the treatment agent except for water. From the viewpoint of suppressing the absorption and desorption of moisture of paper under the environment of high humidity or low humidity, the content of the component (B) is most preferably 0.4% by mass or more.

In the paper treatment agent according to the present invention, even if a component (B), which has a thickening effect when mixed in a polyhydric alcohol such as glycerin, is mixed in an anionic surfactant of component (C), an agent that has low viscosity and high stability, and capable of performing uniform application on paper can be obtained, and the unique texture of paper when the paper is pressed strongly against the skin due to the action of the component (B) and the effect of suppressing the absorption and desorption of moisture of paper under the environment of high humidity or low humidity can be developed. Further, the softness of paper, and the uniform application on paper of paper treatment agent being involved in the development of the texture of paper and the suppression of absorption and desorption of moisture of paper become favorable.

As the anionic surfactant, it is not particularly limited, and an anionic surfactant of a phosphoric acid ester salt type, a sulfonic acid salt type, a sulfuric ester salt type, a carboxylic acid salt type, or the like can be used. These may be used singly alone or in combination of two or more kinds thereof.

Examples of the anionic surfactant of a phosphoric acid ester salt type include alkyl phosphate, alkylaryl ether phosphate, fatty acid amide ether phosphate, and polyoxyalkylene alkyl ether phosphate.

Examples of the anionic surfactant of a sulfonic acid salt type include alkane sulfonate, α-olefin sulfonate, α-sulfo fatty acid methyl ester salt, acyl isethionate, alkyl glycidyl ether sulfonate, alkyl sulfosuccinate, polyoxyalkylene alkyl sulfosuccinate, alkyl benzene sulfonate, alkyl naphthalene sulfonate, N-acyl methyl taurate, formalin condensation sulfonate, paraffin sulfonate, alkyl amide sulfonate, alkenyl amide sulfonate, alkyl glyceryl ether sulfonate, and alkyl aryl ether sulfonate.

Examples of the anionic surfactant of a sulfuric ester salt type include alkyl sulfate, alkenyl sulfate, alkyl ether sulfate, alkenyl ether sulfate, polyoxyalkylene alkyl ether sulfate, alkyl aryl ether sulfate, fatty acid alkanolamide sulfate, fatty acid monoglyceride sulfate, polyoxyalkylene aliphatic amide ether sulfate, alkyl glyceryl ether sulfate, and sulfated fatty acid alkyl ester.

Examples of the anionic surfactant of a carboxylic acid salt type include fatty acid soap, alkyl ether carboxylate, alkylene alkyl ether carboxylate, fatty acid amide ether carboxylate, acyl lactate, N-acyl glutamate, N-acylalanine salt, N-acyl sarcosine salt, N-acyl-ω-amino acid salt, alkyl sulfoacetate, alkenyl sulfoacetate, alkenyl succinate, rosinate, and naphthenate.

In the paper treatment agent according to the present invention, in consideration that the overall development of respective effects, in particular, the softness of paper, and the uniform application on paper of paper treatment agent being involved in the development of the texture of paper and the suppression of absorption and desorption of moisture of paper, become favorable, the content of the component (C) is preferably 0.05% by mass or more, more preferably 0.1% by mass or more, furthermore preferably 0.2% by mass or more, and particularly preferably 1.2% by mass or more, relative to the whole amount of the treatment agent except for water. Further, the content of the component (C) is preferably 25% by mass or less, more preferably 22.5% by mass or less, and furthermore preferably 19% by mass or less, relative to the whole amount of the treatment agent except for water. From the viewpoint of the softness of paper, the content of the component (C) is most preferably 1.2% by mass or more relative to the whole amount of the treatment agent except for water.

In the paper treatment agent according to the present invention, in consideration of the unique texture of paper when the paper is pressed strongly against the skin, the suppression of absorption and desorption of moisture of paper under the environment of high humidity or low humidity, and the achievement of a more remarkable effect of operability, it is preferred that the content of the component (B) is 0.2 to 20% by mass, and the content of the component (C) is 0.2 to 22.5% by mass, relative to the whole amount of the treatment agent except for water.

In the paper treatment agent according to the present invention, in consideration of the overall development of respective effects including a unique texture of paper when the paper is pressed strongly against the skin, the mass ratio (B/C) of the component (B) to the component (C) is preferably 0.05 to 5. In consideration of the viscosity of agent being involved in the stable and easy operability, and the achievement of the favorable uniform application on paper of paper treatment agent being involved in the development of the texture of paper and the suppression of absorption and desorption of moisture of paper, the mass ratio (B/C) of the component (B) to the component (C) is preferably 0.33 or less. In particular, in consideration of the achievement of the more favorable uniform application on paper of a paper treatment agent to paper, it is preferred that the mass ratio (B/C) of the component (B) to the component (C) is 0.33 or less, and further the content of the component (C) is 1.2% by mass or more relative to the whole amount of the treatment agent except for water. In consideration of the achievement of the low viscosity and the more stable and easier operability, it is preferred that the mass ratio (B/C) of the component (B) to the component (C) is 0.33 or less, and further the content of the component (A) is 90% by mass or more relative to the whole amount of the treatment agent except for water.

In the present invention, other components except for the above components can be added as raw materials into a paper treatment agent within the range not impairing the effects of the present invention. As such other components, it is not particularly limited, and examples of such other components include water, a nonionic surfactant, a cationic surfactant, an amphoteric surfactant, an oily component, a thickening agent, an antifungal agent, an antiseptic agent, an antifoaming agent, a fragrance, pigments, a pH adjusting agent, extracts, an antioxidant, an anti-inflammatory agent, an inorganic mineral, an inorganic salt, and a water-soluble polymer.

The amount of the water to be added is not particularly limited, and is preferably added so that the water content in a paper treatment agent is 1 to 30% by mass, more preferably added so that the water content in a paper treatment agent is 3 to 25% by mass, and furthermore preferably added so that the water content in a paper treatment agent is 5 to 20% by mass.

Examples of the nonionic surfactant include a sorbitan fatty acid ester, a polyoxyethylene sorbitan fatty acid ester, a polyoxyethylene fatty acid ester, polyoxyethylene hydrogenated castor oil, polyoxyethylene castor oil, a polyoxyethylene hydrogenated castor oil fatty acid ester, a castor oil fatty acid ester, a hydrogenated castor oil fatty acid ester, an ethylene glycol fatty acid ester, a sucrose fatty acid ester, a glycerin fatty acid ester, a diglycerin fatty acid ester, a polyglycerin fatty acid ester, an organic acid monoglyceride, a polyethylene glycol fatty acid monoethanolamide, a propylene glycol fatty acid ester, a polyoxyethylene lanolin alcohol ether, a polyoxyethylene alkyl ether, a lauric acid alkanolamide, a polyoxyethylene glycerin fatty acid ester, a polyoxyethylene hydrogenated castor oil pyroglutamic acid fatty acid diester, a pyroglutamic acid fatty acid glyceryl, a polyoxyethylene glyceryl pyroglutamic acid fatty acid diester, and a polyether-modified silicone.

Examples of the cationic surfactant include a quaternary ammonium salt such as a monoalkyltrimethylammonium salt, a dialkyldimethylammonium salt, N,N-dialkyloyloxyethyl-N-methyl, an N-hydroxyethylammonium salt, or a stearyl dimethyl benzyl ammonium salt, an alkylpyridinium salt, and an alkyl amine salt.

Examples of the amphoteric surfactant include alkylbetaine, fatty acid amide propyl betaine, lauryl hydroxy sulfobetaine, 2-alkyl-N-carboxymethyl-N-hydroxyethyl imidazolinium betaine, lecithin, hydrogenated lecithin, alkyloxy hydroxypropyl arginine hydrochloride, lauryl hydroxysultaine, lauriminodipropionic acid, sodium undecyl hydroxyethyl imidazolinium betaine, sodium laurylaminodiacetate, lauryl dimethylamino acetic acid betaine, N-[3-alkyloxy-2-hydroxypropyl]-L-arginine hydrochloride, alkyl hydroxy sulfobetaine, alkyl dimethylamine oxide, sodium alkylaminodipropionate, dihydroxyalkyl methylglycine, and sodium lauryldiaminoethylglycinate.

Examples of the oily component include hydrocarbons such as solid paraffin, and liquid paraffin, fats and oils, esters, silicone oils, waxes, and steroids. These may be used singly alone or in combination of two or more kinds thereof.

The paper treatment agent according to the present invention can be produced by mixing respective raw materials uniformly with each other in accordance with a conventional method, and for example, can be obtained by stirring and mixing respective raw materials with each other at a temperature at which the raw materials are dissolved.

In the paper treatment agent according to the present invention, a component (B) may be uniformly mixed by a component (C) into a component (A), and the paper treatment agent may be in a state in which a component (B) and a component (C) are dissolved, solubilized, emulsified, or dispersed in a component (A) being a main component.

By treating paper with the paper treatment agent according to the present invention, the texture of the paper can be improved. In particular, by treating paper with the paper treatment agent according to the present invention, a slippery feeling of paper that is developed by pressure on the paper is improved.

Examples of the paper include tissue paper, toilet paper, facial tissue, pocket tissue, a paper handkerchief, and a paper towel.

The basis weight of paper is preferably 1 to 50 g/m$^3$, and more preferably 5 to 20 g/m$^3$. The ply number (the number of base paper layers) is preferably 1 to 5, and more preferably 2 to 3.

As the method for treating paper with a paper treatment agent, for example, a method for applying a paper treatment agent onto paper can be mentioned. As the method for applying a paper treatment agent onto paper, for example, transcription, spraying, or the like can be mentioned. As the system for applying a paper treatment agent onto paper by these methods, for example, a flexographic printing system, a gravure printing system, a spray system, a rotor dampening system, or the like can be mentioned. In a flexographic printing system, a flexographic printing machine that is one of letterpress printing machines is used, and a paper treatment agent is transferred onto paper by a roller equipped with a machine plate made of rubber or synthetic resin whose surface has been engraved. In a gravure printing system, a gravure printing machine that is one of intaglio printing machines is used, and a paper treatment agent is transferred onto paper by a roller equipped with a cylinder made of metal whose surface has been subjected to platemaking. In a spray system, a paper treatment agent is sprayed onto paper in the form of a mist from a nozzle by compressed air. In a rotor dampening system, a paper treatment agent is sprayed onto paper in the form of a mist by a disk rotating at a high speed.

The amount of a paper treatment agent to be applied onto paper is preferably 1 to 7 g/m$^2$, and more preferably 1.5 to 6 g/m$^2$.

Examples

Hereinafter, the present invention is further described in more detail by way of Examples, however, the present invention is not limited to these Examples.
1. Preparation of Sample
(1) Preparation of Paper Treatment Agent A paper treatment agent was prepared according to the following procedures.

Respective compounding raw materials were charged into a beaker in the amounts described in Tables 1 to 3, and stirred and mixed with each other at a temperature at which the raw materials were dissolved, and thus a paper treatment agent was prepared. The amounts of the components to be mixed, which are shown in Tables 1 to 3, indicate the amounts except for water when the raw materials contain water. The content of water indicates the water content (% by mass) in the paper treatment agent.

In Table 3, as for the respective raw materials, a water-soluble neutral polysaccharide as the water-soluble polymer, polyethylene glycol having an average molecular weight of 4000 as the water-soluble wax, and 2-methyl-dodecyl alcohol as the branched alcohol were used.
(2) Preparation of Treated Paper A treating liquid that the amounts of the component except for water is 25% by mass was prepared by dissolving in water the paper treatment agent obtained by the method described above. Each of the treating liquids was uniformly sprayed so that the component except for water of treatment agent was 25% by mass±3% on both surfaces of dry tissue (having the ply number of 2, and a basis weight of (12 to 13) g/m$^2$), and coated paper of each of Examples 1 to 22 and Comparative Examples 1 to 11 was prepared. After that, the coated paper was air dried for 3 hours, left to stand in a constant temperature and humidity chamber (having a temperature of 25° C. and at a humidity of 40% R.H.) until the moisture content reached equilibrium, and then the obtained coated paper was subjected to evaluation.
(3) Evaluation With respect to the coated paper of each of Examples 1 to 22 and Comparative Examples 1 to 11 and the paper treatment agent, which were prepared in the above, the following evaluations were performed.

First, evaluation for the slippery feeling of paper to be developed by pressure on the paper was performed by sensory evaluation by panelists and by MIU difference (MIU: average friction coefficient) using a test instrument (Table 1 to Table 3). At the same time, as shown in Table 4, for the difference between the slippery feeling of paper to be developed by pressure on the paper, being a "unique slippery feeling" of paper, and the "slippery feeling" and "smoothness" of paper, which have been studied on conventional moisturizing tissues, evaluation was performed by using Example 11, and Comparative Examples 4 and 5 as representative examples.
[Slippery Feeling to be Developed by Pressure (Sensory Evaluation)]

As for the sensory evaluation, coated paper prepared in a similar manner as in the case of the coated paper used for the measurement of MIU difference described later was evaluated as a score of any one of 1 to 3 by 10 skilled panelists on the basis of the following evaluation point, and by using the average value, the evaluation was performed on the basis of the following criteria.
Evaluation Point
3 points: Specific strong slip is felt when paper is pressed strongly.
2 points: Slightly specific slip is felt when paper is pressed strongly.
1 point: Slippery feeling does not change depending on the strength of pressure of fingers.
Evaluation Criteria
⊚: Average score of 10 panelists is 2.5 points or more.
○: Average score of 10 panelists is 2.0 points or more and less than 2.5 points.
Δ: Average score of 10 panelists is 1.5 points or more and less than 2.0 points.
x: Average score of 10 panelists is less than 1.5.
[Slippery Feeling to be Developed by Pressure (MIU Difference)]

With the use of a roughness and friction tester, KES-SE-SR-U (manufactured by KATO TECH CO., LTD.) as a test instrument, the MIU was determined by tracing the surface of one set (two sheets) of coated paper with a friction element. By the difference in the MIU under the conditions that the load and the moving speed of the friction element were 25 g and 10 mm/sec, and 50 g and 1 mm/sec, evaluation for the unique slippery feeling of paper was performed.
Evaluation Criteria
⊚+: Difference in MIU is 0.02 or more.
⊚: Difference in MIU is 0.01 or more and less than 0.02.
○: Difference in MIU is 0.01 or more and less than 0.005
Δ: Difference in MIU is 0.00 or more and less than 0.005
x: Difference in MIU is less than 0.00

Note that in consideration of the range of the numerical values represented by one symbol, the evaluation was performed on a five-point scale, and within the range of the symbol Δ, values of the difference in the MIU, which were close to the upper limit, were evaluated as Δ+.

The results of the sensory evaluation and the evaluation of MIU difference are shown in Tables 1 to 3.

Next, as shown in Table 4, for the difference between the slippery feeling of paper to be developed by pressure on the paper, being a "unique slippery feeling" of paper, and the "slippery feeling" and "smoothness" of paper, evaluation was performed by using Example 11, and Comparative Examples 4 and 5 as representative examples.

With respect to each coated paper, the MIU (average friction coefficient) and the MMD (average deviation of friction coefficient) were measured at a load of and a moving speed of a friction element of 25 g and 10 mm/sec respectively as the condition of light touch, 50 g and 1 mm/sec respectively as the condition of strong touch, and 25 g and 1 mm/sec respectively as the standard condition, and the difference between the values under the condition of light touch and the condition of strong touch was measured.

The MIU is an average value of friction coefficient μ, and is correlated with the slipperiness and slip resistance of paper, which are felt when the surface is rubbed, and as the value of MIU is smaller, the paper becomes easier to slip. The MMD is a degree of fluctuation, that is, how much from the MIU the values fluctuate in the process of tracing the surface of coated paper with a friction element, and is correlated with the smoothness and roughness of paper, which are felt when the surface is rubbed, and as the value of MMD is smaller, the surface becomes smoother and less rough. As the difference between the MIU values under the condition of light touch and the condition of strong touch is larger, the paper has a more unique slippery feeling.

Measurement results in the above are shown in Table 4. With regard to the MIU value that is an index of "slippery feeling" of paper, the MIU values of Example 11 and Comparative Example 4 when the load and moving speed of the friction element were 25 g and 1 mm/sec, respectively were equivalent to each other, but with regard to the difference in MIU that is an index of "unique slippery feeling" of paper, the difference in the friction coefficients (MIU) under the conditions that the load and moving speed of the friction element were 25 g and 10 mm/sec, respectively, and 50 g and 1 mm/sec, respectively, was largely different. Further, the MMD values of Example 11 and Comparative Example 5, which are each an index of "smoothness" of paper, were equivalent to each other, but the difference in MIU that is an index of "unique slippery feeling" of paper was largely different. According to this, it has been confirmed that the slippery feeling of paper to be developed by pressure on the paper, which is a "unique slippery feeling", is different from a "slippery feeling" or "smoothness".

In addition, in Table 4, sensory evaluation was performed for the slippery feeling of paper to be developed by pressure on the paper, the slippery feeling, and the smoothness. The slippery feeling of paper to be developed by pressure on the paper was evaluated on the basis of the criteria similar to that in the above. The slippery feeling, and the smoothness were evaluated on the basis of the following criteria.
(Slippery Feeling)

The evaluation was performed by the average value of 10 panelists under similar conditions as those of the above-described "slippery feeling to be developed by pressure (sensory evaluation)" except that the evaluation point and evaluation criteria were as follows.
Evaluation Point
3 points: Slipping is felt.
2 points: Slipping is slightly felt.
1 point: No slipping is felt.
(Smoothness)

The evaluation was performed by the average value of 10 panelists under similar conditions and criteria as those of the above-described "slippery feeling developed by pressure (sensory evaluation)" except that the evaluation point was as follows.
Evaluation Point
3 points: Smoothness is felt.
2 points: Smoothness is slightly felt.
1 point: No smoothness is felt.
Evaluation Criteria
⊚: Average score of 10 panelists is 2.5 points or more.
○: Average score of 10 panelists is 1.5 points or more and less than 2.5 points.
x: Average score of 10 panelists is less than 1.5 points.

Evaluation results in the above are shown in Table 4. The "slippery feeling" and the "smoothness" were evaluated as ⊚ or ○ in all of Example 11 and Comparative Examples 4 and 5, but in contrast, the "slippery feeling to be developed by pressure" was evaluated as ⊚ in Example 11, and as x in both of Comparative Examples 4 and 5, and it can be understood that there is a great difference in the relative difference in the same item. According to this, similarly to the measurement results of MIU and MMD, it has been confirmed that the slippery feeling of paper to be developed by pressure on the paper, which is a "unique slippery feeling", is different from the "slippery feeling" or the "smoothness".

Next, on the coated paper of each of Examples 1 to 22 and Comparative Examples 1 to 11, the following evaluation was performed for each of the items of suppression of absorption and desorption of moisture of coated paper, uniform application on paper of a paper treatment agent, operability (viscosity) of a paper treatment agent, and softness of coated paper.
[Suppression of Absorption and Desorption of Moisture]

The following tests for moisture absorption and moisture desorption were performed. Five sets (10 sheets) of the coated paper conditioned by being placed at a humidity of 40% R.H. for 24 hours were left to stand at a humidity of 70% R.H. for 24 hours (step of moisture absorption), subsequently, left to stand at 40% R.H. for 24 hours (step of moisture desorption), and during this time period, the mass changes of coated paper caused by the moisture absorption and the moisture desorption were measured. The water content ratio of the coated paper was calculated by the following equation.

Water content ratio (%) of coated paper={(Water content of coated paper)/(Absolute dry mass of coated paper)}×100     [Mathematical Formula 1]

The suppression of moisture desorption was evaluated by the change in the water content ratio between the coated paper immediately after the start of the step of moisture desorption and the coated paper 4 hours after the start of the step of moisture desorption. If the decrease in moisture is slow in the step of moisture absorption or in the step of moisture desorption, there is an effect of suppressing absorption and desorption of moisture.

[Suppression of Moisture Absorption]
Evaluation Criteria
⊚: Difference in the water content ratio between the coated paper immediately after the start of the step of moisture absorption and the coated paper 3 hours after the start of the step of moisture absorption is less than 5%.
○: Difference in the water content ratio between the coated paper immediately after the start of the step of moisture absorption and the coated paper 3 hours after the start of the step of moisture absorption is 5% or more and less than 6%.
Δ: Difference in the water content ratio between the coated paper immediately after the start of the step of moisture absorption and the coated paper 3 hours after the start of the step of moisture absorption is 6% or more and less than 8%.
x: Difference in the water content ratio between the coated paper immediately after the start of the step of moisture absorption and the coated paper 3 hours after the start of the step of moisture absorption is 8% or more.

Note that in consideration of the range of the numerical values represented by one symbol, the evaluation was performed on a five-point scale, and within the range of the symbol Δ, values of the water content ratio, which were close to the lower limit, were evaluated as Δ+.

[Suppression of Moisture Desorption]
Evaluation Criteria
⊚: Difference in the water content ratio between the coated paper immediately after the start of the step of moisture desorption and the coated paper 4 hours after the start of the step of moisture desorption is less than 4%.
○: Difference in the water content ratio between the coated paper immediately after the start of the step of moisture desorption and the coated paper 4 hours after the start of the step of moisture desorption is 4% or more and less than 5%.
Δ: Difference in the water content ratio between the coated paper immediately after the start of the step of moisture desorption and the coated paper 4 hours after the start of the step of moisture desorption is 5% or more and less than 8%.
x: Difference in the water content ratio between the coated paper immediately after the start of the step of moisture desorption and the coated paper 4 hours after the start of the step of moisture desorption is 8% or more.

Note that in consideration of the range of the numerical values represented by one symbol, the evaluation was performed on a five-point scale, and within the range of the symbol Δ, values of the water content ratio, which were close to the lower limit, were evaluated as Δ+.

[Uniform Application]
With the use of a roughness and friction tester, KES-SE-SR-U (manufactured by KATO TECH CO., LTD.) as the test instrument, the friction coefficient (MIU) was determined at three places for each set (two sheets) of sample of coated paper of 10×10 cm by tracing the surface of the sample of coated paper with a friction element. The uniform application on paper was evaluated by the standard deviation of the MIU values at the three places.

Evaluation Criteria
⊚: Standard deviation of MIU values at three places is less than 0.010.
○: Standard deviation of MIU values at three places is 0.010 or more and less than 0.015.
Δ: Standard deviation of MIU values at three places is 0.015 or more and less than 0.020.
x: Standard deviation of MIU values at three places is 0.020 or more.

[Operability (Viscosity)]
With respect to the treatment agents of Examples 1 to 22 and Comparative Examples 1 to 11 prepared in the above, the viscosity was measured at 60 rpm and 40° C. by using a Brookfield viscometer, and evaluated on the basis of the following criteria.

Evaluation Criteria
⊚: Viscosity of treatment agent is less than 500 mPa·s.
0: Viscosity of treatment agent is 500 mPa·s or more and less than 2000 mPa·s.
x: Viscosity of treatment agent is 2000 mPa·s or more or is unmeasurable (uniform state cannot be retained).

[Softness]
As for the sensory evaluation, the coated paper was evaluated as a score of any one of 1 to 3 by 10 skilled panelists on the basis of the following evaluation point, and by using the average value, the evaluation was performed on the basis of the following criteria.

Evaluation Point
3 points: Extremely soft
2 points: Soft
1 point: Slightly hard

Evaluation Criteria
⊚: Average score of 10 panelists is 2.5 points or more.
○: Average score of 10 panelists is 2.0 points or more and less than 2.5 points.
Δ: Average score of 10 panelists is 1.5 points or more and less than 2.0 points.
x: Average score of 10 panelists is less than 1.5 points.

The composition of each of Examples and Comparative Examples and evaluation results of each of the items are shown in Tables 1 to 3. The results regarding the difference between the above-described slippery feeling of paper to be developed by pressure on the paper, which is a "unique slippery feeling", and the "slippery feeling", and the "smoothness" are shown in Table 4. In respective evaluation items of Tables 1 to 3, the symbols ⊚+, ⊚, and ○ are desirable in view of solving problems, and there is a significant difference between the symbols Δ and ⊚ and between the symbols ⊚ and ○ in developing effects. The symbol Δ cannot be said to be not necessarily desirable in view of solving problems, and in particular, in a case where all of the three of "slippery feeling to be developed by pressure", the "suppression of moisture absorption", and "suppression of absorption and desorption of moisture" are not any of the symbols ⊚+, ⊚, and ○, it was determined to be improper in view of solving problems. In a case where the symbol x is included even in one of the respective items, it was determined to be improper in view of solving problems.

TABLE 1

| | | Example | | | | | | | | | | |
|---|---|---|---|---|---|---|---|---|---|---|---|---|
| | | 1 | 2 | 3 | 4 | 5 | 6 | 7 | 8 | 9 | 10 | 11 |
| Polyhydric alcohol (A) | Glycerin | 400 | 400 | 400 | 400 | 3233 | 400 | 3233 | 300 | 4900 | 300 | 900 |
| | Sorbitol | | | | | | | | | | | |
| Straight chain alcohol or straight chain fatty acid (B) | Tridecyl alcohol | | | | | | | | | | | |
| | Stearyl alcohol | | | | | | | | | | | |
| | Cetylstearyl alcohol | 50 | 1 | 99 | 5 | 5 | 50 | 5 | 10 | 5 | 50 | 20 |
| | Oleyl alcohol | | | | | | | | | | | |
| | Stearic acid | | | | | | | | | | | |

TABLE 1-continued

| | | Example | | | | | | | | | | |
|---|---|---|---|---|---|---|---|---|---|---|---|---|
| | | 1 | 2 | 3 | 4 | 5 | 6 | 7 | 8 | 9 | 10 | 11 |
| Anionic surfactant (C) | Phosphoric acid ester salt type | 10 | 99 | 1 | 95 | 5 | 30 | 30 | 90 | 5 | 30 | 80 |
| | Sulfonic acid salt type | | | | | | | | | | | |
| | Sulfuric ester salt type | | | | | | | | | | | |
| | Carboxylic acid salt type | | | | | | | | | | | |
| Other components | Nonionic surfactant (Sucrose fatty acid ester) | | | | | | | | | | | |
| | Nonionic surfactant (POE sorbitan fatty acid ester) | | | | | | | | | | | |
| | Nonionic surfactant (POE alkyl ether) | 40 | | | | | 20 | 20 | | | 20 | |
| | Cationic surfactant (Quaternary ammonium salt type) | | | | | | | | | | | |
| | Liquid paraffin | | | | | 90 | | 45 | | 90 | | |
| | Water-soluble polymer | | | | | | | | | | | |
| | Water-soluble wax | | | | | | | | | | | |
| | Branched alcohol (B') (2-Methyl-dodecyl alcohol) | | | | | | | | | | | |
| | Hydroxylated soybean phospholipid | | | | | | | | | | | |
| | Triethanolamine | | | | | | | | | | | |
| | Polyether-modified silicone | | | | | | | | | | | |
| | Paraoxybenzoic acid ester | | | | | | | | | | | |
| | Dimethyl silicone | | | | | | | | | | | |
| Whole amount | | 500 | 500 | 500 | 500 | 3333 | 500 | 3333 | 400 | 5000 | 400 | 1000 |
| Content of component (A) (% by mass) | | 80.0 | 80.0 | 80.0 | 80.0 | 97.0 | 80.0 | 97.0 | 75.0 | 98.0 | 75.0 | 90.0 |
| Content of component (B) (% by mass) | | 10.0 | 0.2 | 19.8 | 1.0 | 0.2 | 10.0 | 0.2 | 2.5 | 0.1 | 12.5 | 2.0 |
| Content of component (C) (% by mass) | | 2.0 | 19.8 | 0.2 | 19.0 | 0.2 | 6.0 | 0.9 | 22.5 | 0.1 | 7.5 | 8.0 |
| Component (B)/Component (C) | | 5.0 | 0.01 | 99 | 0.05 | 1.0 | 1.7 | 0.17 | 0.11 | 1.0 | 1.7 | 0.25 |
| Content of nonionic surfactant (% by mass) | | 8.0 | 0 | 0 | 0 | 0 | 4.0 | 0.6 | 0 | 0 | 5.0 | 0 |
| Branched alcohol or branched fatty acid (B')/component (B) | | 0.0 | 0.0 | 0.0 | 0.0 | 0.0 | 0.0 | 0.0 | 0.0 | 0.0 | 0.0 | 0.0 |
| Content of water (% by mass) | | 10.0 | 10.0 | 10.0 | 10.0 | 10.0 | 10.0 | 10.0 | 10.0 | 10.0 | 10.0 | 10.0 |
| Evaluation | Slippery feeling to be developed by pressure (Sensory evaluation) | ◎ | ◎ | ◎ | ◎ | ◎ | ◎ | ◎ | ◎ | ○ | ◎ | ◎ |
| | Slippery feeling to be developed by pressure (MIU difference) | ◎+ | ◎ | ◎+ | ◎+ | ◎ | ◎+ | ◎ | ◎+ | ○ | ◎+ | ◎+ |
| | Suppression of moisture absorption | ◎ | ○ | ◎ | ◎ | ○ | ◎ | ○ | ◎ | ○ | ◎ | ◎ |
| | Suppression of moisture desorption | ◎ | ○ | ◎ | ◎ | ○ | ◎ | ○ | ◎ | ○ | ◎ | ◎ |
| | Uniform application (Standard deviation) | ○ | ◎ | ○ | ◎ | ○ | ○ | ○ | ◎ | ○ | ○ | ◎ |
| | Operability (Viscosity) | ○ | ○ | ○ | ○ | ○ | ○ | ◎ | ○ | ○ | ○ | ◎ |
| | Softness | ◎ | ◎ | ○ | ◎ | ○ | ◎ | ○ | ◎ | ○ | ◎ | ◎ |

TABLE 2

| | | Example | | | | | | | | | | |
|---|---|---|---|---|---|---|---|---|---|---|---|---|
| | | 12 | 13 | 14 | 15 | 16 | 17 | 18 | 19 | 20 | 21 | 22 |
| Polyhydric alcohol (A) | Glycerin | 2400 | 1900 | 97 | 900 | 900 | 900 | | 900 | 900 | 400 | 400 |
| | Sorbitol | | | | | | | 900 | | | | |
| Straight chain alcohol or straight chain fatty acid (B) | Tridecyl alcohol | | | | | | | | | | | 0.58 |
| | Stearyl alcohol | | | 2 | | | | | | | | |
| | Cetylstearyl alcohol | 10 | | | 20 | 20 | 20 | 20 | 20 | 20 | | |
| | Oleyl alcohol | | | | | | | | | | 1 | |
| | Stearic acid | | 20 | | | | | | | | | |
| Anionic surfactant (C) | Phosphoric acid ester salt type | 30 | 30 | 5 | | | | 80 | 80 | 80 | 99 | 99 |
| | Sulfonic acid salt type | | | | 80 | | | | | | | |
| | Sulfuric ester salt type | | | | | 80 | | | | | | |
| | Carboxylic acid salt type | | | | | | 80 | | | | | |

TABLE 2-continued

|  |  | Example | | | | | | | | | | |
|---|---|---|---|---|---|---|---|---|---|---|---|---|
|  |  | 12 | 13 | 14 | 15 | 16 | 17 | 18 | 19 | 20 | 21 | 22 |
| Other components | Nonionic surfactant (Sucrose fatty acid ester) | | | | | | | | | | | |
|  | Nonionic surfactant (POE sorbitan fatty acid ester) | | | | | | | | | | | |
|  | Nonionic surfactant (POE alkyl ether) | 20 | 20 | 1 | | | | | | | | |
|  | Cationic surfactant (Quaternary ammonium salt type) | | | | | | | | | | | |
|  | Liquid paraffin | 40 | 30 | | | | | | | | | |
|  | Water-soluble polymer | | | | | | | | | | | |
|  | Water-soluble wax | | | | | | | | | | | |
|  | Branched alcohol (B') (2-Methyl-dodecyl alcohol) | | | | | | | | | | | 0.42 |
|  | Hydroxylated soybean phospholipid | | | | | | | | | | | |
|  | Triethanolamine | | | | | | | | | | | |
|  | Polyether-modified silicone | | | | | | | | | | | |
|  | Paraoxybenzoic acid ester | | | | | | | | | | | |
|  | Dimethyl silicone | | | | | | | | | | | |
| Whole amount | | 2500 | 2000 | 105 | 1000 | 1000 | 1000 | 1000 | 1000 | 1000 | 500 | 500 |
| Content of component (A) (% by mass) | | 96.0 | 95.0 | 92.4 | 90.0 | 90.0 | 90.0 | 90.0 | 90.0 | 90.0 | 80.0 | 80.0 |
| Content of component (B) (% by mass) | | 0.4 | 1.0 | 1.9 | 2.0 | 2.0 | 2.0 | 2.0 | 2.0 | 2.0 | 0.2 | 0.1 |
| Content of component (C) (% by mass) | | 1.2 | 1.5 | 4.8 | 8.0 | 8.0 | 8.0 | 8.0 | 8.0 | 8.0 | 19.8 | 19.8 |
| Component (B)/Component (C) | | 0.33 | 0.67 | 0.40 | 0.25 | 0.25 | 0.25 | 0.25 | 0.25 | 0.25 | 0.01 | 0.01 |
| Content of nonionic surfactant (% by mass) | | 0.8 | 1.0 | 1.0 | 0 | 0 | 0 | 0 | 0 | 0 | 0 | 0 |
| Branched alcohol or branched fatty acid (B')/component (B) | | 0.0 | 0.0 | 0.0 | 0.0 | 0.0 | 0.0 | 0.0 | 0.0 | 0.0 | 0.0 | 0.7 |
| Content of water (% by mass) | | 10.0 | 10.0 | 10.0 | 10.0 | 10.0 | 10.0 | 10.0 | 1.0 | 50.0 | 10.0 | 10.0 |
| Evaluation | Slippery feeling to be developed by pressure (Sensory evaluation) | ⊚ | ⊚ | ⊚ | ⊚ | ⊚ | ⊚ | ⊚ | ⊚ | ⊚ | ○ | ○ |
|  | Slippery feeling to be developed by pressure (MIU difference) | ⊚+ | ⊚+ | ⊚+ | ⊚+ | ⊚+ | ⊚+ | ⊚+ | ⊚+ | ⊚+ | ○ | ○ |
|  | Suppression of moisture absorption | ⊚ | ⊚ | ⊚ | ⊚ | ⊚ | ⊚ | ⊚ | ⊚ | ⊚ | ○ | ○ |
|  | Suppression of moisture desorption | ⊚ | ⊚ | ⊚ | ⊚ | ⊚ | ⊚ | ⊚ | ⊚ | ⊚ | ○ | ○ |
|  | Uniform application (Standard deviation) | ⊚ | ○ | ○ | ⊚ | ⊚ | ⊚ | ⊚ | ⊚ | ⊚ | ⊚ | ○ |
|  | Operability (Viscosity) | ⊚ | ○ | ○ | ⊚ | ⊚ | ⊚ | ○ | ⊚ | ⊚ | ⊚ | ⊚ |
|  | Softness | ⊚ | ⊚ | ⊚ | ⊚ | ⊚ | ⊚ | ○ | ⊚ | ⊚ | ⊚ | ○ |

TABLE 3

|  |  | Comparative Example | | | | | | | | | | |
|---|---|---|---|---|---|---|---|---|---|---|---|---|
|  |  | 1 | 2 | 3 | 4 | 5 | 6 | 7 | 8 | 9 | 10 | 11 |
| Polyhydric alcohol (A) | Glycerin | 400 | 93 | 400 | 97.7 | 96 | 400 | 97 | 10 | 0 | 400 | 81 |
|  | Sorbitol | | | | | | | | 2 | | | 5 |
| Straight chain alcohol or straight chain fatty acid (B) | Tridecyl alcohol | | 1.5 | | | | | | | | | |
|  | Stearyl alcohol | | | | | | | 2 | | 20 | | |
|  | Cetylstearyl alcohol | | | | | 1 | | | | | 1 | |
|  | Oleyl alcohol | | | | | | | | | | | 1 |
|  | Stearic acid | | | | | | | | 0.1 | | | |
| Anionic surfactant (C) | Phosphoric acid ester salt type | 99 | | 100 | 2.2 | 2.5 | | | | | | |
|  | Sulfonic acid salt type | | | | | | | | | | | |
|  | Sulfuric ester salt type | | 1 | | | | | | | | | |
|  | Carboxylic acid salt type | | | | | | | | | | | |
| Other components | Nonionic surfactant (Sucrose fatty acid ester) | | | | | | | | | 80 | | |
|  | Nonionic surfactant (POE sorbitan fatty acid ester) | | 2 | | | | | 1 | | | 6 | |
|  | Nonionic surfactant (POE alkyl ether) | | | | | | | | 99 | 0.2 | | |

TABLE 3-continued

| | | Comparative Example | | | | | | | | | | |
|---|---|---|---|---|---|---|---|---|---|---|---|---|
| | | 1 | 2 | 3 | 4 | 5 | 6 | 7 | 8 | 9 | 10 | 11 |
| | Cationic surfactant (Quaternary ammonium salt type) | | | | | | | | | | 99 | 2 |
| | Liquid paraffin | | | | | 1.5 | | 1 | | | | |
| | Water-soluble polymer | | | | 0.1 | | | | | | | |
| | Water-soluble wax | | | | | | | 1 | | | | |
| | Branched alcohol (B') (2-Methyl-dodecyl alcohol) | 1 | 1.5 | | | | | | | | | |
| | Hydroxylated soybean phospholipid | | 1 | | | | | | | | | |
| | Triethanolamine | | | | | | | | 0.05 | | | |
| | Polyether-modified silicone | | | | | | | | 0.1 | | | |
| | Paraoxybenzoic acid ester | | | | | | | | 0.01 | | | |
| | Dimethyl silicone | | | | | | | | | | | 0.01 |
| Whole amount | | 500 | 100 | 500 | 100 | 100 | 500 | 100 | 14.46 | 100 | 500 | 95.01 |
| Content of component (A) (% by mass) | | 80.0 | 93.0 | 80.0 | 97.7 | 96.0 | 80.0 | 97.0 | 83.0 | 0 | 80.0 | 90.5 |
| Content of component (B) (% by mass) | | 0 | 2 | 0 | 0 | 0 | 0.2 | 2.0 | 0.7 | 20.0 | 0.2 | 1.1 |
| Content of component (C) (% by mass) | | 19.8 | 1.0 | 20.0 | 2.2 | 2.5 | 0 | 0 | 0 | 0 | 0 | 0 |
| Component (B)/Component (C) | | 0 | 2 | 0 | 0 | 0 | — | — | — | — | — | — |
| Content of nonionic surfactant (% by mass) | | 0 | 2.0 | 0 | 0 | 0 | 19.8 | 1.0 | 1.4 | 80.0 | 0 | 6.3 |
| Branched alcohol or branched fatty acid (B')/component (B) | | — | 1.0 | — | — | — | 0.0 | 0.0 | 0.0 | 0.0 | 0.0 | 0.0 |
| Content of water (% by mass) | | 10.0 | 10.0 | 10.0 | 10.0 | 10.0 | 10.0 | 10.0 | 40.1 | 10.0 | 10.0 | 5.0 |
| Evaluation | Slippery feeling to be developed by pressure (Sensory evaluation) | Δ | Δ | X | X | X | X | X | X | X | Δ | Δ |
| | Slippery feeling to be developed by pressure (MIU difference) | Δ | Δ | X | X | X | X | X | X | X | Δ+ | Δ |
| | Suppression of moisture absorption | Δ | Δ | X | X | X | X | X | X | X | Δ+ | Δ |
| | Suppression of moisture desorption | Δ | Δ | X | X | X | X | X | X | X | Δ+ | Δ |
| | Uniform application (Standard deviation) | ◎ | ○ | ◎ | ○ | ○ | X | X | X | X | Δ | Δ |
| | Operability (Viscosity) | ◎ | ◎ | ○ | ◎ | ◎ | X | X | X | X | ○ | ○ |
| | Softness | ○ | ○ | ◎ | ○ | ○ | X | X | ○ | X | Δ | Δ |

TABLE 4

| | | Condition of light touch | | Condition of strong touch | | Difference between measurement values | | Standard condition | | Sensory evaluation | | |
|---|---|---|---|---|---|---|---|---|---|---|---|---|
| | Adhesion | 25 g, 10 mm/sec | | 50 g, 1 mm/sec | | under both conditions | | 25 g, 1 mm/sec | | Slippery feeling | | |
| Agent No. | amount (% by mass) | MIU value | MMD value | MIU value | MMD value | MIU value difference | MMD value difference | MIU value | MMD value | to be developed by pressure | Slippery feeling | Smoothness |
| Example 11 | 23.7 | 0.213 | 0.0083 | 0.189 | 0.0047 | 0.024 | 0.0043 | 0.206 | 0.0051 | ◎ | ○ | ○ |
| Comparative Example 4 | 23.8 | 0.213 | 0.0080 | 0.223 | 0.0062 | −0.009 | 0.0032 | 0.211 | 0.0062 | X | ◎ | ○ |
| Comparative Example 5 | 25.4 | 0.260 | 0.0093 | 0.266 | 0.0049 | −0.006 | 0.0042 | 0.239 | 0.0055 | X | ○ | ◎ |

In Tables 1 to 3, Examples 11 and 12 had the most favorable evaluation in all items of the "slippery feeling to be developed by pressure", the "suppression of absorption and desorption of moisture", the "uniform application", the "operability (viscosity)", and the "softness".

In this regard, it can be understood that as for the "slippery feeling to be developed by pressure", the sensory evaluation and the MIU difference are correlated with each other in overall Examples 1 to 22 and Comparative Examples 1 to 11.

Although the content of water was changed to 1.0% by mass and 50.0% by mass in Examples 19 and 20, respectively, from the content of water in Example 11, Examples 19 and 20 both had the most favorable evaluation in all items similarly as in Example 11.

In Example 18, the component (A) was changed from glycerin of Example 11 to sorbitol in the same amount as that of the glycerin of Example 11. The "slippery feeling to be developed by pressure", the "suppression of absorption and desorption of moisture", and the "uniform application" in Example 18 were equivalent to those in a case of the glycerin, and the "operability (viscosity)", and the "softness" were favorable in a case of the glycerin among the components (A).

In Example 13, the composition was set similar to that in Example 12 except that the component (B) was changed from cetylstearyl alcohol of Example 12 to stearic acid. The "slippery feeling to be developed by pressure", the "suppression of absorption and desorption of moisture", and the "softness" in Example 13 were equivalent to those in Example 12, and the "uniform application", and the "operability (viscosity)" were more favorable in Example 12 using cetylstearyl alcohol.

In Example 14, the composition was set similar to that in Example 11 except that the component (B) was changed from cetylstearyl alcohol in Example 11 to stearyl alcohol, and a nonionic surfactant was mixed. The "slippery feeling to be developed by pressure", the "suppression of absorption and desorption of moisture", and the "softness" in Example 14 were equivalent to those in Example 11, and the "uniform application", and the "operability (viscosity)" were more favorable in Example 11 using cetylstearyl alcohol.

In Examples 1 to 12, mainly, the contents of the component (B) and the component (C), and the ratio of the component (B) to the component (C) were changed.

From the comparison among Example 9, Examples 2, 5, and 7, and Example 12, if the content of the component (B) is 0.2% by mass or more, and further 0.4% by mass or more, relative to the whole amount of the treatment agent except for water, the "slippery feeling to be developed by pressure" becomes more remarkable. If the content of the component (B) is 0.4% by mass or more, the "suppression of absorption and desorption of moisture" becomes more remarkable.

From the comparison between Examples 3, 5, 7, and 9, and Example 12, if the content of the component (C) is 1.2% by mass or more relative to the whole amount of the treatment agent except for water, the "softness" becomes more remarkable.

From the comparison between Example 9 and Examples 1 to 8, and 10 to 12, if the content of the component (B) is 0.2 to 20% by mass, and the content of the component (C) is 0.2 to 22.5% by mass, relative to the whole amount of the treatment agent except for water, the overall evaluation for respective items is more remarkably improved.

From the comparison between Examples 1, 3, 5, 6, 9, and 10, and Example 12, if the mass ratio (B/C) of the component (B) to the component (C) is 0.33 or less, the "uniform application", and the "operability (viscosity)" becomes more remarkable. Further, from the comparison with Example 7, if the mass ratio (B/C) of the component (B) to the component (C) is 0.33 or less, and further the content of the component (C) is 1.2% by mass or more relative to the whole amount of the treatment agent except for water, the "uniform application" becomes more remarkable. From the comparison with Examples 2, 4, 6, 8, and 10, if the mass ratio (B/C) of the component (B) to the component (C) is 0.33 or less, and further the content of the component (A) is 90% by mass or more relative to the whole amount of the treatment agent except for water, the "operability (viscosity)" becomes more remarkable. From the comparison among Example 2, Examples 1 and 4, and other Examples, if the mass ratio (B/C) of the component (B) to the component (C) is 0.05 to 5, the overall evaluation for respective items including particularly the "slippery feeling to be developed by pressure" is more remarkably improved.

In Comparative Examples 1 to 5, formulation in which the component (A) and the component (C) had been mixed, but mainly the component (B) has not been mixed was adopted. In Comparative Example 1, a branched alcohol (B') had been mixed in place of the component (B), but the "slippery feeling to be developed by pressure" and "suppression of absorption and desorption of moisture" as in those in Examples 1 to 22 in which a straight chain alcohol or a straight chain fatty acid had been mixed as the component (B) were not obtained. In Comparative Example 2, a straight chain alcohol (B) and a branched alcohol (B') had been mixed at a mass ratio of 1:1, but similarly, the "slippery feeling to be developed by pressure" and the "suppression of absorption and desorption of moisture" were not obtained.

In this regard, in Example 22, a straight chain higher alcohol (B) and a branched alcohol (B') were mixed so that the mass ratio (B'/B) was less than 1. When Example 22 is compared with Example 2 in which the same kind and same amount of components (A) and (C) had been mixed as those in Example 22, and further the component (B) had been only mixed, the "slippery feeling to be developed by pressure" showed a decreasing tendency, but was within the acceptable range. As for Comparative Examples 3 to 5, in the results in cases where a water-soluble polymer (Comparative Example 4), and liquid paraffin (Comparative Example 5) were each mixed together with an anionic surfactant (C), the "slippery feeling to be developed by pressure", and the "suppression of absorption and desorption of moisture" were evaluated as the lowest in both of the cases.

In Comparative Examples 6 to 8, 10, and 11, formulation in which the component (A) and the component (B) had been mixed, but the component (C) had not been mixed was adopted. In Comparative Example 9, formulation in which the component (B) had been mixed, but the component (A) and the component (C) had not been mixed was adopted. In Comparative Examples 6 to 9, a nonionic surfactant, and the component (B) had been mixed, but the "slippery feeling to be developed by pressure", and the "suppression of absorption and desorption of moisture" were evaluated as the lowest, and the "uniform application", and the "operability (viscosity)" were also evaluated as the lowest in all of the cases. In Comparative Example 8, liquid paraffin of oil component and water-soluble wax had been mixed, although the softness was improved, the other items were similar to those in Comparative Examples 6, 7, and 9. In a case of the composition in which water-soluble wax having high viscosity had been used, improvement in the "uniform application" and the "operability (viscosity)" was not observed. In Comparative Examples 10 and 11, a cationic surfactant, or a cationic surfactant and a nonionic surfactant had been mixed in place of the component (C), and when compared with Comparative Examples 6 to 9, although there is a tendency of improvement in the overall respective evaluations, evaluations as ○, ⊚, and ⊚+, which were observed in overall Examples 1 to 22, were not obtained.

The invention claimed is:

1. A paper treatment agent, comprising
   50% by mass or more of a polyhydric alcohol (A) relative to the whole amount of the agent except for water as a main component,
   at least one component (B) selected from the group consisting of a straight chain alcohol and a straight chain fatty acid, and
   an anionic surfactant (C), and
   optionally at least one component (B') selected from the group consisting of a branched alcohol and a branched fatty acid, wherein a mass ratio (B'/B) of the component (B') to the component (B) is less than 1,
   wherein
   a content of the component (B) is 0.2 to 20% by mass, relative to the whole amount of the treatment agent except for water, and
   a content of the component (C) is 1.2 to 22.5% by mass, relative to the whole amount of the treatment agent except for water.

2. The paper treatment agent according to claim 1, wherein
   a mass ratio (B/C) of the component (B) to the component (C) is 0.05 to 5.

3. The paper treatment agent according to claim 1, wherein
   the number of carbon atoms of the component (B) is 12 to 22.

4. A method for improving a slippery feeling of paper to be developed by pressure on the paper, comprising
treating the paper with the paper treatment agent according to claim 1.

* * * * *